United States Patent [19]

Arroyo

[11] Patent Number: 4,837,279

[45] Date of Patent: Jun. 6, 1989

[54] BONE CEMENT

[75] Inventor: Nestor A. Arroyo, East Windsor, N.J.

[73] Assignee: Pfizer Hospital Products Corp, Inc., New York, N.Y.

[21] Appl. No.: 158,472

[22] Filed: Feb. 22, 1988

[51] Int. Cl.[4] ........................ A61L 25/00; C08L 31/02
[52] U.S. Cl. .................................... 525/193; 525/937; 523/116; 523/117; 523/118
[58] Field of Search ....................... 523/116, 117, 118; 525/309, 937, 193

[56] References Cited

U.S. PATENT DOCUMENTS

| | | | |
|---|---|---|---|
| 3,715,331 | 2/1973 | Molnar | 523/117 |
| 4,093,576 | 6/1978 | de Wijn | 260/17 R |
| 4,268,639 | 5/1981 | Seidel et al. | 525/303 |
| 4,341,691 | 7/1982 | Anuta | 523/116 |
| 4,490,497 | 12/1984 | Evrard | 523/116 |
| 4,500,658 | 2/1985 | Fox | 523/117 |
| 4,554,686 | 11/1985 | Baker | 623/16 |
| 4,588,583 | 5/1986 | Pietsch | 523/116 |

FOREIGN PATENT DOCUMENTS

| | | |
|---|---|---|
| 0218471 | 4/1987 | European Pat. Off. . |
| 1532318 | 11/1978 | United Kingdom . |
| 1533283 | 11/1978 | United Kingdom . |
| 1349259 | 4/1984 | United Kingdom . |
| 2156824 | 10/1985 | United Kingdom . |

*Primary Examiner*—Lewis T. Jacobs
*Assistant Examiner*—David Buttner
*Attorney, Agent, or Firm*—Peter C. Richardson; Lawrence C. Akers; Robert F. Sheyka

[57] ABSTRACT

There is disclosed a bone cement composition comprising (a) a liquid component comprising a monomer of an acrylic ester and (b) a powdered component comprising, based on the weight of the powdered component,
(i) from 0 to about 20 percent of a methyl methacrylate homopolymer,
(ii) from about 30 to about 60 percent of a methyl methacrylate-styrene copolymer, and
(iii) from about 30 to about 60 percent of a methyl methacrylate-butyl methacrylate copolymer.

8 Claims, No Drawings

BONE CEMENT

BACKGROUND OF THE INVENTION

The present invention relates to a bone cement composition. More particularly, the present invention relates to a bone cement wherein the liquid component comprises a monomer of an acrylic ester and the powdered component comprises a combination of two or three acrylate polymers.

Bone cements find wide usage in a variety of applications. For instance, they are used for cementing implants in place, for the anchoring of endoprostheses of the joints, in the treatment of skull defects, and for the performance of spinal fusion. These cements are typically polymeric materials and the surgeon usually mixes the interactive components to make the cement at an appropriate stage during the surgical procedure. Typically, the components of the bone cement comprise a powdered homopolymer or copolymer of methyl methacrylate and a suitable liquid monomer, for example, methyl methacrylate. To accelerate the polymerization of the bone cement, a catalyst system may also be used. The catalyst, if present, is in the form of a redox catalyst system, usually containing an organic peroxy compound, such as dibenzoyl peroxide, plus a reducing component, such as p-toluidine.

Once the bone cement/implant combination, for example, is in the body, the surgeon will later wish to inspect the implant by X-rays and since the polymers and/or monomers are relatively radiolucent, radiopaque materials, also called opacifiers, are added to the polymeric bone cement. Examples of such opacifiers are barium salts, such as barium sulphate, and other salts such as zirconium oxide and zinc oxide. While these opacifying agents give the necessary radiopacity, it has been reported that they tend to reduce the mechanical properties, e.g. transverse strength and compressive strength of the set polymeric bone cement. The reported solution to this alleged problem of reduced mechanical strength is disclosed in a number of patents.

U.S. Pat. No. 4,500,658 describes a method of incorporating an opacifier in an acrylic resin by suspension polymerization.

EPO Patent Application No. 0218471 discloses a composition for forming a bone cement comprising a powder component and a monomer component, the powder component comprising ethyl methacrylate polymer beads incorporating particles of opacifier therein and the monomer component comprising n-butyl methacrylate.

U.S. Pat. No. 4,341,691 discloses a low viscosity bone cement comprising a liquid methyl methacrylate monomer and powdered polymethylmethacrylate beads wherein 85-95% of the polymethylmethacrylate beads fall through a #40 mesh and #100 mesh screen and 5-15% of the polymethylmethacrylate beads pass through a #40 mesh screen but not through a #100 mesh screen.

U.S. Pat. No. 4,554,686 discloses a frozen polymethylmethacrylate bone cement.

U.S. Pat. No. 4,268,639 discloses a bone cement prepared by mixing a finely powdered solid polymer phase of polymethyl methacrylate and/or poly(2-hydroxyethyl methacrylate) with a liquid monomer phase of methyl methacrylate and/or 2-hydroxyethyl methacrylate in a weight ratio of polymer phase to monomer phase of 1.5 to 3.3.:1.

United Kingdom Pat. No. 1,532,318 discloses a bone cement comprising a liquid component comprising methyl methacrylate as an emulsion in water and a powdered component comprising polymethylmethacrylate in finely divided form.

The existing bone cement compositions are usually hand mixed at the time of surgery resulting in materials with a maximum tensile strength of approximately 30 MPa and a maximum tensile deformation of approximately 0.015 strain. With the introduction of new methods of mixing the cement such as vacuum mixing and centrifugation, improvements in the tensile strength of the bone cement have been reported. While useful for their intended purpose, it would also be highly desirable to have a bone cement composition exhibiting higher maximum tensile deformation, that is, the ability to sustain higher strains without failure.

SUMMARY OF THE INVENTION

In accordance with the present invention, there is disclosed a bone cement composition comprising:
 (a) a liquid component comprising a monomer of an acrylic ester, and
 (b) a powdered component comprising, based on the weight of the powdered component,
  (i) from 0 to about 20 percent of a methyl methacrylate homopolymer,
  (ii) from about 30 to about 60 percent of a methyl methacrylate-styrene copolymer, and
  (iii) from about 30 to about 60 percent of a methyl methacrylate-butyl methacrylate copolymer.

Additional agents such as free radical stabilizers, for example, hydroquinone, and polymerization accelerators, such as, for example, N,N-dimethyl paratoluidine, may also be incorporated in component (a).

In a preferred embodiment, the bone cement composition is essentially free of component (b)(i) and components (b)(ii) and (b)(iii) are each present at about 50 percent by weight.

Opacifying agents can also be incorporated in the powdered component.

In a further embodiment, the present invention is directed to a powdered component useful as a precursor for a bone cement composition comprising, based on the weight of the powdered component,
 (a) from 0 to about 20 percent of a methyl methacrylate homopolymer,
 (b) from about 30 to about 60 percent of a methyl methacrylate-styrene copolymer, and
 (c) from about 30 to about 60 percent of a methyl methacrylate-butyl methacrylate copolymer.

The present invention is also directed to a process for the production of a bone cement composition comprising combining:
 (a) a liquid component comprising a monomer of an acrylic ester with
 (b) a powdered component comprising, based on the weight of the powdered component,
  (i) from 0 to about 20 percent of a methyl methacrylate homopolymer,
  (ii) from about 30 to about 60 percent of a methyl methacrylate-styrene copolymer,
  (iii) from about 30 to about 60 percent of a methyl methacrylate-butyl methacrylate copolymer.

In another embodiment, the present invention is directed to a process for the production of a powdered component useful as a precursor for a bone cement composition comprising combining, (a) from 0 to about 20 percent of a methyl methacrylate homopolymer, (b) from about 30 to about 60 percent of a methyl methacrylate-styrene copolymer, and (c) from about 30 to about 60 percent of a methyl methacrylate-butyl methacrylate copolymer.

DETAILED DESCRIPTION OF THE INVENTION

Component (a) of the bone cement composition of the present invention comprises a liquid monomer of an acrylic ester. By the term "acrylic ester" is meant the acrylates, preferably having a $C_1$-$C_4$ alkyl group in the ester moiety. One especially preferred acrylic ester is methacrylate with an especially preferred liquid monomer being methyl methacrylate. This liquid monomer is represented by the formula:

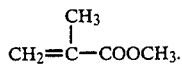

In addition, the liquid monomer may contain a polymerization acceleration such as N,N-dimethyl paratoluidine. Additionally, the liquid monomer may also contain a free radical stabilizer such as hydroquinone. The hydroquinone functions to prevent premature polymerization which may occur under conditions such as heat, light or chemical reagents.

The powdered component of the bone cement composition is a blend of three acrylic polymers and comprises the following three components:

(i) from 0 to about 20 percent of a methyl methacrylate homopolymer, (ii) from about 30 to about 60 percent of a methyl methacrylate-styrene copolymer, and (iii) from about 30 to about 60 percent of a methyl methacrylate-butyl methacrylate copolymer.

Component (i), if added, is encompassed by the formula:

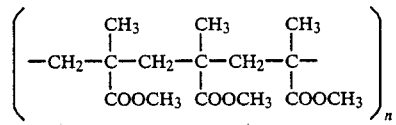

and preferably, the methyl methacrylate homopolymer has a weight average molecular weight of from about 3,000,000 to about 3,500,000. The particle size distribution in the methyl methacrylate homopolymer can range from about 50 to about 250 micron.

Component (ii) comprises from about 30 to about 60 percent of a methyl methacrylate-styrene copolymer. Especially preferred are those copolymers having a weight average molecular weight of from about 300,000 to about 400,000. The particle size distribution in the methyl methacrylate styrene copolymer can range from about 30 to about 90 micron.

Component (iii) comprises from about 30 to about 60 percent of a methyl methacrylate-butyl methacrylate copolymer. Especially preferred are those copolymers having a weight average molecular weight of from about 500,000 to about 600,000. The particle size distribution in the methyl methacrylate-butyl methacrylate copolymer can range from about 45 to about 120 micron.

The powdered component may also contain an opacifying agent. The opacifying agent may be selected from any of those known for this purpose. Representative examples include barium sulphate, zinc oxide and zirconium oxide. Preferably, the opacifying agent will be added at a concentration of from about 5 to about 10 percent of the powdered component.

Additional agents, such as colorants, extra catalysts, antibiotics, etc., may also be added to the powder component.

Liquid component (a) and powdered component (b) are combined under sterile conditions to yield the bone cement composition. Preferred methods of sterilization include irradiation, especially for the powder component, and bacteriological filtration for the liquid monomer.

Although the present invention has been described in relation to the combination of liquid component (a) and powdered component (b) to form a bone cement composition, it will be apparent to those skilled in the art that powdered component (b) comprising (i) from 0 to about 20 percent of a methyl methacrylate homopolymer, (ii) from about 30 to about 60 percent of a methyl methacrylate-styrene copolymer, and (iii) from about 30 to about 60 percent of a methyl methacrylate-butyl methacrylate copolymer, also forms a part of the present invention.

The present invention is also directed to a process for the production of the bone cement composition of the present invention. The bone cement composition is formed by combining (a) the liquid component previously described with (b) the three component powder component previously described. The order of addition of each component to form the bone cement composition is not critical although it is usually preferred to add the liquid component to the powder component.

In addition, the present invention also embraces a process for the production of a powdered component useful as a precursor for a bone cement composition. The powdered component is made by combining (a) from 0 to about 20 percent of a methyl methacrylate homopolymer, (b) from about 30 to about 60 percent of a methyl methacrylate-styrene copolymer, and (c) from about 30 to about 60 percent of a methyl methacrylate-butyl methacrylate copolymer. The three components may be combined using conventional techniques to yield the powdered component.

Having described the invention in general terms, reference is now made to specific examples thereof. It is to be understood that these examples are not meant to limit the present invention, the scope of which is determined by the appended claims.

EXAMPLE 1

Two bone cement compositions were made by combining the two components as follows.

| | Formulation A | |
|---|---|---|
| (a) | Methyl methacrylate | 20 ml |
| (b)(i) | Poly methylmethacrylate | 0 g |
| (b)(ii) | Methyl methacrylate-styrene copolymer | 20 g |
| (b)(iii) | Methyl methacrylate-butyl methacrylate copolymer | 20 g |
| | Formulation B | |

-continued

| | | | |
|---|---|---|---|
| (a) | Methyl methacrylate | 20 ml | |
| (b)(i) | Poly methylmethacrylate | 0 g | |
| (b)(ii) | Methyl methacrylate-styrene | 16 g | |
| (b)(iii) | Methyl methacrylate-butyl methacrylate | 24 g | |

The compositions were allowed to set and were then tested against control Simplex P for their resistance to stress and strain. Other formulations as seen in Table 1, were also tested.

DESCRIPTION OF TENSILE TEST

The axial tensile properties of these materials are determined according to ASTM-D-638-72 (Standard Method of Test For Tensile Properties of Plastics).

SPECIMEN PREPARATIONS

The powder and liquid components are hand mixed for approximately 2 minutes in the barrel of an Exeter ® cement gun. The cement is extruded into aluminum molds where it is allowed to set.

The resulting specimens are standard type IV flat tensile bars.

The tensile bars are aged for seven days in saline solution at 37° C.

TESTING

Testing is carried out at room temperature in an Instron 1122 testing unit with a cross head speed of 5 mm per minute.

Deformation is determined with a 10% maximum elongation extensometer. Strain is calculated from the elongation at failure.

Stress is calculated from the load at failure.

Modulus is calculated from the initial slope of the load versus deformation curve.

The test results were as follows.

TABLE I

| Form.[1] # | Component b(i)[3] | Component b(ii)[3] | Component b(iii)[3] | Stress (MPa) | Δ%* | Strain | Δ%* | Modulus (MPa) | Δ%* |
|---|---|---|---|---|---|---|---|---|---|
| Control | Radiopaque Simplex P | | | 28.3 | | 0.014 | | 2,450 | |
| 1 | 0% | 100.0%[(2)] | 0% | 23.0 | −19 | 0.012 | −14 | 2,000 | −18 |
| 2[4] | 16.7% | 83.3% | 0% | 29.3 | +3.5 | 0.013 | −7 | 2,340 | −4 |
| 3 | 16.75% | 62.5% | 20.75% | 32.6 | +15 | 0.017 | +21 | 2,270 | −7 |
| 4 | 0% | 60.0% | 40.0% | 35.4 | +25 | 0.018 | +28 | 2,480 | +1 |
| 5[5] | 0% | 50.0% | 50.0% | 36.6 | +29 | 0.028 | +100 | 1,570 | −36 |
| 6 | 16.75% | 41.65% | 41.65% | 35.3 | +25 | 0.020 | +43 | 2,050 | −16 |
| 7[6] | 0% | 40.0% | 60.0% | 36.8 | +30 | 0.023 | +64 | 1,980 | −19 |
| 8 | 16.75% | 20.75% | 62.5% | 27.5 | −3 | 0.023 | +64 | 1,560 | −36 |
| 9 | 16.7% | 0% | 83.3% | 25.1 | −11 | 0.024 | +71 | 1,360 | −44 |
| 10 | 0% | 0% | 100.0% | 23.4 | −17 | 0.022 | +57 | 1,260 | −48 |

*Are percentage differences from control.
NOTES:
[1] A formulation consists of 20 ml of liquid methylmethacrylate monomer (component a) and 40 g of powder (component b).
[2] 100% of component b refers to 40 g of powder divided between components b(i), b(ii), and b(iii).
[3] b(i): polymethylmethacrylate
b(ii): styrene - methylmethacrylate copolymer
b(iii): butylmethacrylate - methylmethacrylate copolymer
[4] Formulation #2 is equivalent to Simplex P without BaSO4.
[5] Formulation #5 is described as formulation A of Example 1.
[6] Formulation #7 is described as formulation B of Example 1.

I claim:

1. A bone cement composition comprising:
   (a) a liquid component comprising a monomer of an acrylic ester, and
   (b) a powdered component comprising, based on the weight of the powdered component,
      (i) from 0 to about 20 percent of a methyl methacrylate homopolymer,
      (ii) from about 30 to about 60 percent of a methyl methacrylate-styrene copolymer,
      (iii) from about 30 to about 60 percent of a methyl methacrylate-butyl methacrylate copolymer.
2. The composition of claim 1 further comprising a free radical stabilizer and a polymerization accelerator incorporated in component (a).
3. The composition of claim 2 wherein said free radical stabilizer is hydroquinone and said polymerization accelerator is N,N-dimethyl paratoluidine.
4. The composition of claim 1 wherein component b(i) is present at about 1 to about 20 percent, based on the weight of the powdered component.
5. The composition of claim 1 essentially free of component (b)(i).
6. The composition of claim 5 wherein component (b)(ii) is present at about 50 percent by weight and component (b)(iii) is present at about 50 percent by weight.
7. The composition of claim 1 further comprising an opacifying agent in the powdered component.
8. A process for the production of a bone cement composition comprising combining:
   (a) a liquid component comprising a monomer of an acrylic ester with
   (b) a powdered component comprising, based on the weight of the powdered component,
      (i) from 0 to about 20 percent of a methyl methacrylate homopolymer,
      (ii) from about 30 to about 60 percent of a methyl methacrylate-styrene copolymer,
      (iii) from about 30 to about 60 percent of a methyl methacrylate-butyl methacrylate copolymer.

* * * * *